United States Patent [19]

Awazu et al.

[11] Patent Number: 4,974,591
[45] Date of Patent: Dec. 4, 1990

[54] BIO-PHOTOSENSOR

[75] Inventors: Kunio Awazu; Masahiko Kanda, both of Osaka, Japan

[73] Assignee: Sumitomo Electric Industries, Ltd., Osaka, Japan

[21] Appl. No.: 264,105

[22] Filed: Oct. 28, 1988

[30] Foreign Application Priority Data

| Nov. 2, 1987 | [JP] | Japan | 62-168039[U] |
| Nov. 2, 1987 | [JP] | Japan | 62-168040[U] |
| Nov. 2, 1987 | [JP] | Japan | 62-168041[U] |
| Nov. 2, 1987 | [JP] | Japan | 62-168042[U] |
| Nov. 2, 1987 | [JP] | Japan | 62-168043[U] |
| Nov. 13, 1987 | [JP] | Japan | 62-174189[U] |
| Nov. 13, 1987 | [JP] | Japan | 62-174190[U] |

[51] Int. Cl.$^5$ ................................. A61B 5/00
[52] U.S. Cl. ........................... 128/633; 128/664; 128/666
[58] Field of Search ................. 128/632–633, 128/664–667, 644, 687–690; 356/38–41

[56] References Cited

U.S. PATENT DOCUMENTS

| 3,835,837 | 9/1974 | Peek | 128/666 |
| 4,406,289 | 9/1983 | Wesseling et al. | 128/689 X |
| 4,425,921 | 1/1984 | Fujisaki et al. | 128/644 X |
| 4,621,643 | 11/1986 | New, Jr. et al. | 128/633 |
| 4,685,464 | 8/1987 | Goldberger | 128/664 X |
| 4,825,872 | 5/1989 | Tan et al. | 356/41 X |
| 4,825,879 | 5/1989 | Tan et al. | 128/633 |
| 4,830,014 | 5/1989 | Goodman et al. | 128/666 X |

FOREIGN PATENT DOCUMENTS

| 0287312 | 11/1967 | Australia | 128/666 |
| 2524792 | 10/1983 | France | 128/664 |

Primary Examiner—Max Hindenburg
Assistant Examiner—J. P. Lacyk
Attorney, Agent, or Firm—Armstrong, Nikaido, Marmelstein, Kubovcik & Murray

[57] ABSTRACT

A bio-photosensor used to examine the function of various organs of a human body or the like. It has a flexible printed circuit board (FPC) formed with an electric circuit, a light emitter and a light receptor mounted on the FPC and connected to an electric cable through the electric circuit, and a fixing tape adapted to be put on the FPC applied to a finger or the like to fix it in position. In order to support the emitter and the receptor, a strip of flexible film is used. It can be fitted on the finger comfortably. Pairs of sensors are provided around the light receptor to check if the receptor is put in an exactly opposite position to the emitter when the bio-photosensor is put on the finger. The FPC is provided with a mark at such a position that the emitter and the receptor will be opposed to each other when the bio-photosensor is applied to the finger with the mark in contact with the finger tip.

16 Claims, 5 Drawing Sheets

BIO-PHOTOSENSOR

FIELD OF THE INVENTION

The present invention relates to a bio-photosensor adapted to be fixed to a part of the body of an examinee e.g. a finger to measure the absorption of the light emitted from one side of the finger and transmitted through the finger to the other side.

BACKGROUND OF THE INVENTION

This type of sensor is used e.g. to examine the function of the liver of an examinee. In this examination, a specific pigment which is selectively taken into and excreted from only the liver is injected into the blood stream. Then the concentration of the pigment in blood plasma is measured with the sensor to determine the blood plasma disappearance rate and retention ratio of the pigment to examine the function of the liver.

As one example of such prior art photosensors, there is known a bio-photosensor which is applied to a finger and in which light is transmitted from one side of the finger to the other side so as to detect the fluctuation of transmittance or reflectance of light due to the blood flow. Signals representative of such fluctuations are processed and calculated to obtain such vital information as pulse rates or blood pressures (see Japanese Unexamined Patent Publication No. 60-34432 and Japanese Unexamined Utility Model Publication No. 60-158803).

Figure 1A:
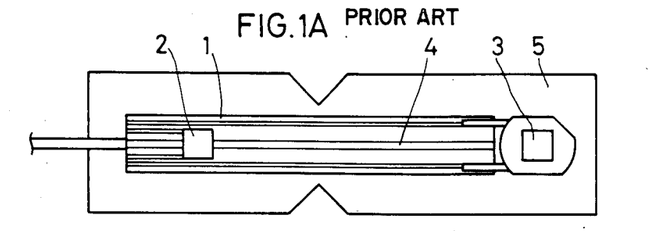
FIG. 1A is a plan view of a prior art bio-photosensor.
Figure 1B:
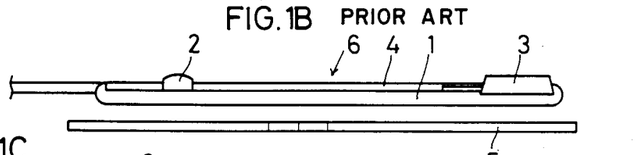
FIG. 1B is a front view of the same.

FIGS. 1A and 1B show a prior art bio-photosensor comprising a strip of flexible base film 1, and a light emitter 2 and a light receptor 3 mounted on the base film 1 and spaced longitudinally from each other. The emitter 2 and the receptor 3 are connected respectively to lead wires 4. An adhesive tape 5 is used to fix the photosensor 6 to a finger.

The base film 1 provided with the emitter 2 and the receptor 3 is applied to a finger 7 in its longitudinal direction and turned back at the finger tip 7a. (FIG. 1C) The tape 5 is then put over the base film 1 to fix the photosensor 6 to the finger 7.

Figure 1C:
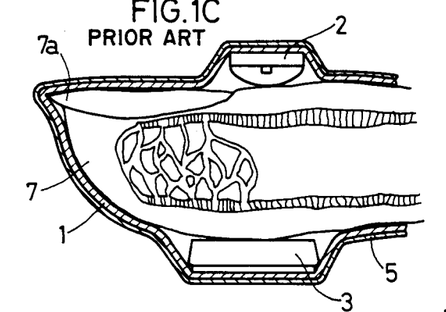
FIG. 1C is a sectional side view of the same fitted on a finger.

In this state, the sensor 6 is turned on to cause the light emitter 2 to give forth light which passes through the finger 7 and strikes the receptor 3. In response thereto, the receptor 3 applies signals to a signal processor (not shown) through the lead wire 4 and a connector (not shown). The processor will process the signals about the fluctuation of light transmittance to obtain vital information such as pulse rate and blood pressure.

In this prior art photosensor, wires are directly connected to the emitter and the receptor and they have to be fixed to the flexible base film. Means and step of fixing the wires to the base film will add to the cost of the photosensor.

Also, the rigidity of lead wires extending in the longitudinal direction of the base film will lower the flexibility of the base film. Such a photosensor could not be comfortably fitted on part of the body of an examinee. Further, there was a fear that the wire or cable might be pulled out of the sensor or be broken at their connections during use only with a small tensile or bending stress which tends to act on the connections.

In FIG. 1C, the emitter 2 and the receptor 3 are set in exactly opposite positions to each other. But if they are not, it is necessary to increase the power of the emitter 2 or the amplifying factor of the receptor 3. If the power of the emitter is increased, the finger might be burned due to a heat buildup of the emitter. An increase in the amplifying factor of the receptor would impair the S/N ratio, thus lowering the accuracy of the photosensor. This problem results from +he fact that the photosensor is not equipped with means for ensuring the relative position between the emitter 2 and the receptor 3 when the photosensor is fitted on the finger.

Such a prior art photosensor is provided on its base film with a light emitter capable of emitting two beams having different wavelengths from each other. However, no photosensor is equipped with a light emitter capable of emitting two beams, one cf the beams having such a wavelength as to be absorbed almost entirely by a specific pigment which is removed exclusively by the hepatic parenchyma once it is injected into the blood and the other having such a wavelength as not to be absorbed by the abovesaid pigment. Elaborate equipment was therefore necessary to measure the absorption of a pigment e.g. in the blood.

SUMMARY OF THE INVENTION

It is an object of the present invention to provide a bio-photosensor which can be fitted on a part of the body of an examinee easily and comfortably.

In accordance with the present invention, there is provided a bio-photosensor comprising a flexible printed circuit board formed with an electric circuit and adapted to be wrapped around a part of the body of an examinee, and a light emitter and a light receptor mounted on the printed circuit board with some distance therebetween so that they will be opposed to each other at both sides of the part of the examinee when the printed circuit board is wrapped therearound, the light emitter and the light receptor being electrically connected through the electric circuit to an electric cable connected to one end of the printed circuit board.

It is another object of the present invention to provide a bio-photosensor which allows the light emitter and the light receptor to be disposed in exactly opposite positions to each other when the bio-photosensor is fitted on a finger or the like.

In accordance with the present invention, there is provided a position displacement detector means which has a pair of sensors in the vicinity of the light receptor to check whether or not the light receptor is exactly opposed to the light emitter.

As another means for this purpose, there is provided a bio-photosensor having a strip of flexible printed circuit board provided with a mark at a portion adapted to be brought into contact with the tip of a fingernail.

In accordance with the present invention, a bio-photosensor is provided which is capable of emitting a plurality of beams having different wavelengths from one another, one of said beams having such a wavelength as to be absorbed by a specific pigment which is removed exclusively by the hepatic parenchyma when it is injected into the blood, and the others having such wavelengths as not to be absorbed in this pigment. In order to accomplish this object, one light emitter comprises a light emitting diode emitting a beam of the first wavelength and another light emitting diode emitting a beam of the second wavelength.

DESCRIPTION OF THE DRAWINGS

Other features and objects of the present invention will become apparent from the following description taken with reference to the accompanying drawings, in which.

DESCRIPTION OF THE PREFERRED EMBODIMENTS

Figure 2A:
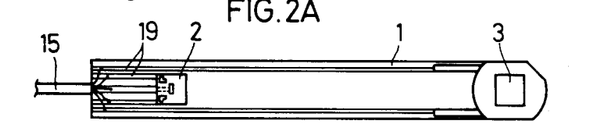
FIG. 2A is a plan view of the first embodiment of the photosensor according to the present invention.
Figure 2B:
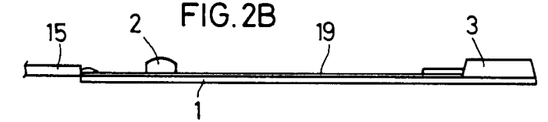
FIG. 2B is a front view of the same.

FIGS. 2A and B show the first embodiment of the present invention in which a flexible printed circuit (hereinafter referred to as FPC) board 1 is etched on its one side with a required electrode pattern (conductor circuit 19). A light emitter 2 and a light receptor 3 are mounted on the FPC board 1 in position and connected to the conductor circuit 19 by soldering. A cable 15 is also connected at one end of the FPC board to the conductor circuit 19 by soldering.

The light emitter 2 is a several-millimeter square chip having two light emitting diodes mounted thereon. The lights emitted from the two diodes have different wavelengths from each other. The transmittance of one of the lights through the body of an examinee is used as a reference on the basis of which the transmittance of the other is measured. Two diodes are used for precise measurement.

As the light receptor 3, a silicon photodiode is used. The cable 15 is a five-core cable, three of the five cores for activating the emitter 2 and the other two for relaying the signals from the receptor 3.

Figure 3:
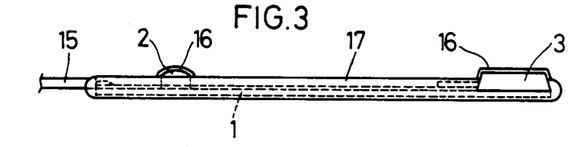
FIG. 3 is a front view of a modification of the first embodiment.

The photosensor in the first embodiment should preferably be provided with protective layers 16 and 17 as shown in FIG. 3. The layer 16 covering the light emitter 2 and the light receptor 3 is made of a transparent resin or glass. The layer 17 covering the other part of the photosensor is made of an insulating and flexible resin such as epoxy, urethane or silicone resin.

The photosensor in this embodiment is applied e.g. to a finger so as to sandwich the finger with the emitter 2 and the receptor 3 opposed to each other at both sides of the finger and fixed in position by means of a fixing tape. The light emitter 2 is then activated to emit two beams of light having different wavelengths from each other. The beams are transmitted through the finger to hit upon the receptor 3. The light beams received on the receptor are analyzed to determine the content of pigment in the blood stream, etc.

In this embodiment, the FPC board is used as supports for the light emitter and the light receptor and they are connected to the cable through the conductor circuit on the FPC board. It is not necessary to mount the cable on FPC so as to extend in its longitudinal direction. It is thus not necessary to apply a tape for fixing the cable to the FPC board, either. The photosensor in this embodiment is more flexible and can be fitted more comfortably on a finger or the like. Further, its reliability is increased and the production cost is reduced.

Figure 4:
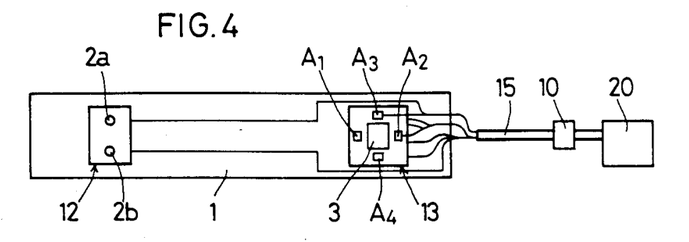
FIG. 4 is a plan view of the second embodiment.

FIG. 4 shows the second embodiment of the present invention in which four position sensors $A_1$ to $A_4$ are provided around the light receptor 3 to determine whether or not the receptor is in an exactly opposite position to the light emitter 2. The sensors $A_1$ and $A_2$ are arranged in front and rear of the receptor 3 to determine whether they are in exactly opposite position in the longitudinal direction of finger and the sensor $A_1$ and $A_4$ are arranged at both sides of the receptor 3 to determine whether they are in an exactly opposite position in the transverse direction of the finger. The light emitting diodes $2a$ and $2b$, the receptor 3 and the four position sensors $A_1$ to $A_4$ are connected to a main body 20 through lead wires 15 and a connector 10.

Figure 5:
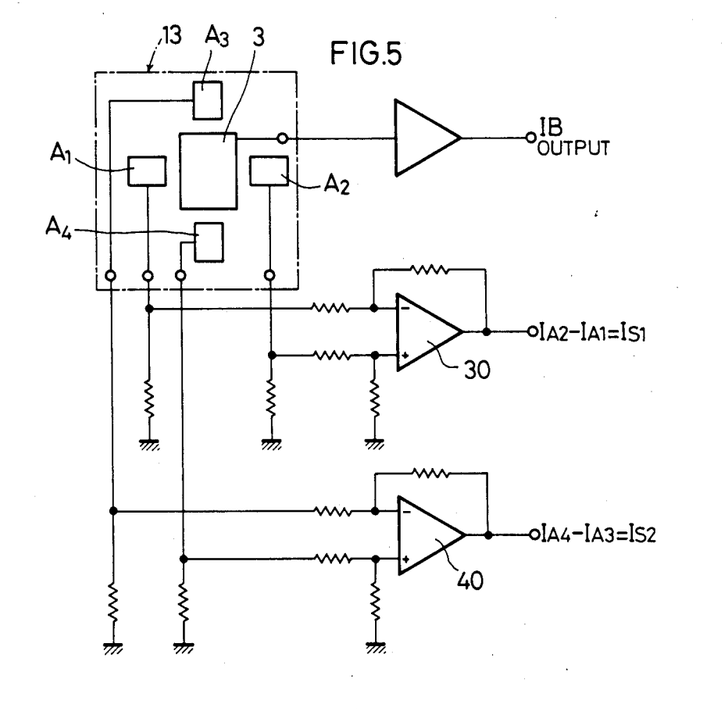
FIG. 5 is a circuit diagram showing how the photosensor of the second embodiment works.

FIG. 5 is a circuit diagram showing how the photosensor of the second embodiment operates. An electric current $IA_1$ which flows through the sensor $A_1$ and a current $IA_1$ which flows through the sensor $A_2$ are compared with each other in an IC comparator 30 to check the position of the receptor 3 in a widthwise direction of the finger. The result is expressed as $IS_1$. Currents $IA_3$ and $IA_4$ which flow through the sensors $A_3$ and $A_4$, respectively, are compared in an IC comparator 40 to check the position of the receptor 3 in a longitudinal direction of the finger. The result is expressed as $IS_2$. The receptor 3 gives an output IB representative of the light transmittance. The position sensors and comparator means such as IC comparators constitute a position displacement detecting means.

If the emitter and the receptor are out of mutually opposite positions, the relationship between the currents $IS_1$ and $IS_2$ will be expressed by the inequality $|IS_1|IS|IS_2| \geq IS_0$, wherein $IS_0$ represents a preset current. In such a case, an alarm may be set off to give a warning to an operator so that he can refit the photosensor to correct the relative position between the emitter and the receptor.

Though in this embodiment, two pairs of position sensors are used, they may be provided in any number of pairs. For example, even one pair would be of a great help in checking the relative position between the emitter and the receptor.

Also, the number of light emitting diodes provided in the emitter is not limited to two but may be one o, three or more.

Any positional displacement between the emitter and the receptor is detected by comparing the electric signals from the position sensors. If any displacement is detected, an operator is notified immediately so that the operator can refit the photosensor so as to arrange the emitter and receptor in exactly opposite positions. Since the emitter and receptor can be positioned exactly in a face-to-face relationship, it is not necessary to increase the power of the emitter to such an extent as to give a burn on the finger. Nor is it necessary to amplify the sensitivity of the receptor which would lower the S/N ratio and thus the precision of the sensor. This will increase the reliability of the bio-photosensor.

Figure 6A:
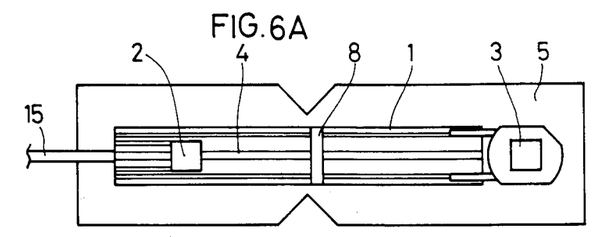
FIG. 6A is a plan view of the third embodiment.
Figure 6B:
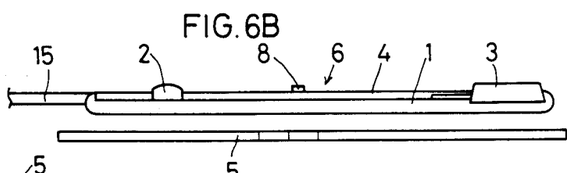
FIG. 6B is a front view of the same.
Figure 7:
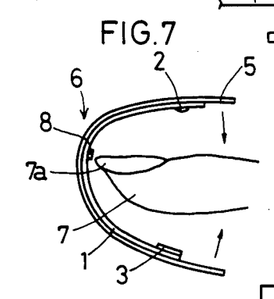
FIG. 7 is a side view of the same showing how it is fitted on a finger.

The third embodiment is shown in FIGS. 6A, 6B and 7. This embodiment is substantially the same as the first embodiment except for the following points.

As shown in FIGS. 6A and 6B, the photosensor is provided with a mark 8 at a position where the tip of the nail of a finger contacts when the photosensor is put on the finger. The mark 8 may be in the form of a projection or a mere flat sign.

Next, it will be described how the bio-photosensor in this embodiment is put on a finger with reference to FIG. 7. The photosensor 6 is applied to a finger 7 so as to extend in its longitudinal direction with the mark 8 in contact with the tip of the fingernail 7a. The photosensor is turned back at the tip of the fingernail. The mark 8 should be provided on the FPC board at such a position that the emitter 2 and the receptor 3 will be put in exactly opposite position to each other when the photosensor 6 is fitted on the finger in the above-described manner.

Figure 8A:
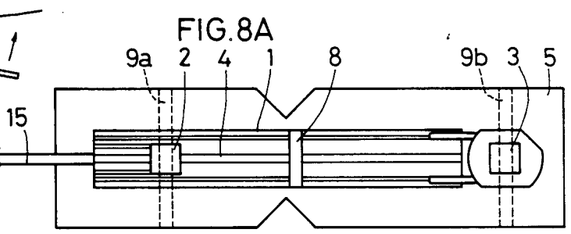
FIG. 8A is a plan view of the fourth embodiment.
Figure 8B:
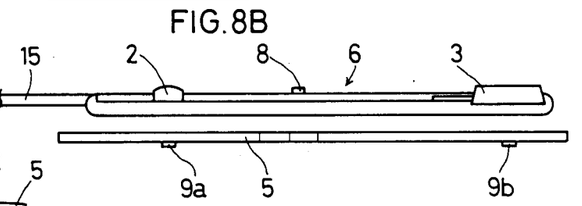
FIG. 8B is a front view of the same.
Figure 8C:
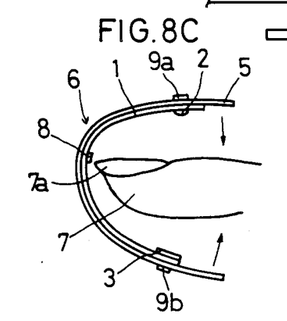
FIG. 8C is a side view of the same showing how it is fitted on a finger.

FIGS. 8A to 8C show the fourth embodiment of the present invention which is a modification of the third embodiment. The mark 8 in the third embodiment serves as a mere standard for the relative position between the emitter and the receptor because the shape and length of the nail and finger differ from person to person. In this embodiment, besides the mark 8, second marks 9a and 9b are provided on the fixing tape 5 on its back side so as to be located right behind the emitter 2 and the receptor 3, respectively. They may be projections or mere flat marks.

Next, it will be described how the photosensor of the fourth embodiment is applied to a finger with reference to FIG. 8C. After bringing the mark 8 into contact with the tip of the fingernail 7a as in the third embodiment, the photosensor 6 is turned back so as to wrap the finger 7 in its longitudinal direction. The emitter 2 and the receptor 3 can be put in exactly opposite positions to each other by aligning the mark 9a located right behind the emitter 2 with the mark 9b located right behind the receptor 3. Then the photosensor is fixed in position. The second marks 9a and 9b will thus allow the emitter and the receptor to be put in right positions irrespective of the length of the nail and the shape of the finger.

Figure 9A:
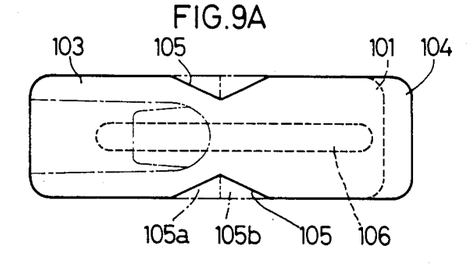
FIG. 9A is a plan view of the fixing tape of the photosensor of the fifth embodiment of the present invention.
Figure 9B:
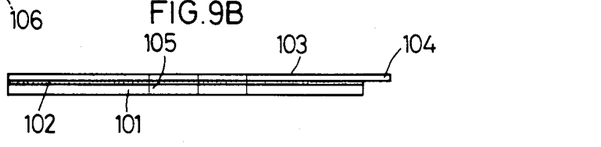
FIG. 9B is a front view of the same.
Figure 11:
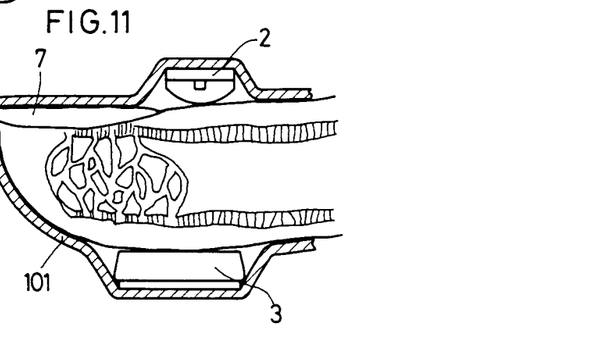
FIG. 11 is a sectional view of the fifth embodiment showing how it is fitted on a finger.

FIGS. 9A and 9B show the fixing tape used in the fifth embodiment of the present invention. The fixing tape 5 comprises a substrate 101, an adhesive layer 102 bonded to one side of the substrate 101, a release paper 103 laminated on the adhesive layer 102. The release paper 103 has a tab portion 104 and is formed with cutouts 105 at both sides so as to be opposed to each other. The cutouts 105 are used as a positioning mark then applying the photosensor to a finger of an examinee. Namely, the emitter and the receptor are mounted on the finger so as to oppose to each other when the photosensor is put on the finger with its cutouts 105 at the tip of the finger, as shown in FIG. 11. But, it is required that the emitter and the receptor are exactly positioned with respect to the substrate 101. For this purpose, the substrate 101 is provided on its surface behind the emitter and the receptor with a printed mark 106 so as to indicate the positions of the emitter and the receptor.

The cutouts 105 serve also to form voids 105a and 105b as shown in FIG. 9A. If no voids 105a and 105b are formed, these portions may stick together when the substrate 101 is put on the finger, thus pressing the finger so tightly as to cause it to be congested with blood.

Figure 10:
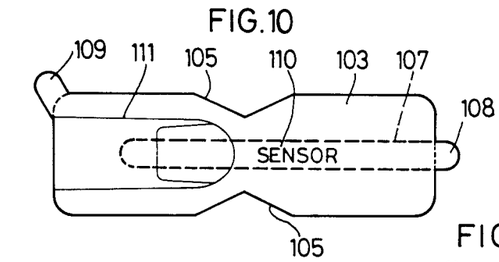
FIG. 10 is a plan view of the release paper of the photosensor of the sixth embodiment.

FIG. 10 shows the sixth embodiment in which the release paper 103 in the fifth embodiment is modified. Namely, it is formed with a perforated weak line 107 which outlines a portion on which the emitter and the receptor are to be mounted. The perforated line 107 may be replaced with a half-cut line or a continuous through-cut line. A tab 108 is provided at one end of the portion enclosed in the perforated line 107. Another tab 109 is provided at a desired portion along the edge of the release paper 103 and outside the portion enclosed in the line 107. Further, on the release paper 103, there are printed letters 110 which indicate the positions of the emitter and the receptor and a mark 111 which indicates the mounting position of a part (a finger in the drawing) of the body of the examinee. The same mark 111 should be printed on one side of the substrate 101, too, at a position corresponding to the mark on the release paper 103.

Figure 12:
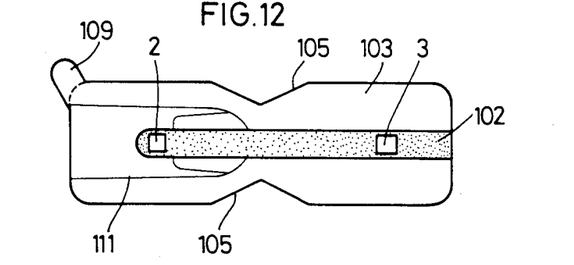
FIG. 12 is a plan view of the fixing tape cf the sixth embodiment with the release paper partially peeled off.

In use, the release paper 103 is peeled firstly only at the portion enclosed in the weak line 107 to expose a part of the adhesive layer 102 as shown in FIG. 12. Then the emitter and the receptor are stuck in position on the exposed part of the adhesive layer 103. Next, the remainder of the release paper is peeled off. Thus, the emitter and the receptor can be mounted in exact positions easily. Since the adhesive layer 102 is covered with the release paper 103 except the portion enclosed in the weak line 107, until right before the tape is applied to the finger, its bonding strength is kept high.

Figure 13A:
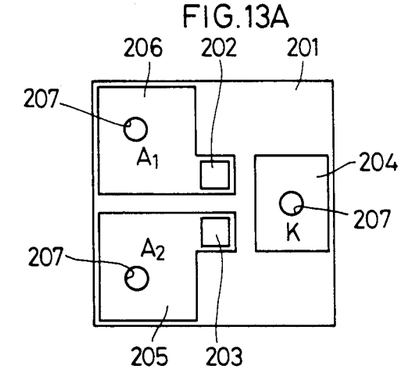
FIG. 13A is a plan view of the multi-wavelength light emitter used in the bio-photosensor of the seventh embodiment with the cover removed.
Figure 13B:
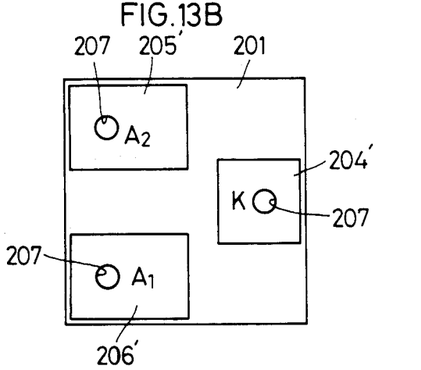
FIG. 13B is a bottom view of the same.
Figures 14, 15, 16:
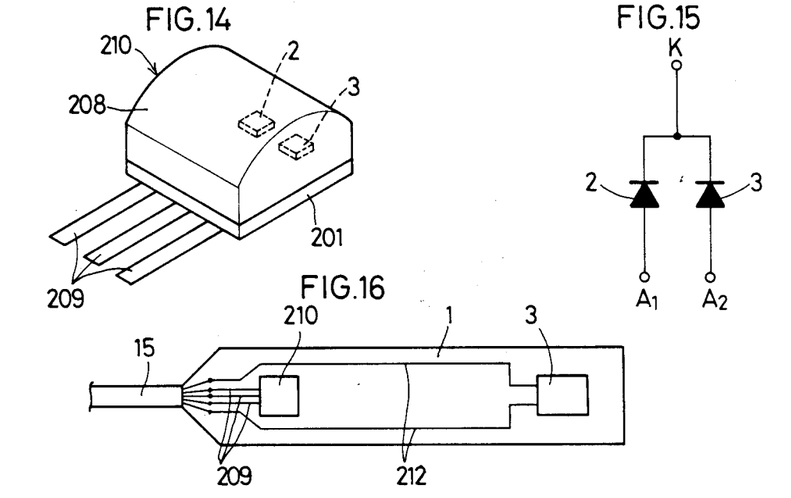
FIG. 14 is a perspective view of the multi-wavelength light emitter.
FIG. 15 is a block diagram of the same.
FIG. 16 is a plan view of the seventh embodiment equipped with the multi-wavelength light emitter of FIG. 14.

FIGS. 13A, 13B, and 14 show an example of the light emitter used in the present invention. A multiwavelength light emitter 210 (FIG. 14) includes a glass-epoxy board 201 having its entire surface except the electrodes subjected to etching. Light emitting diodes 202 and 203 having different wavelengths are connected to a common cathode 204 and to anodes 205 and 206, respectively. The light emitting diodes 202 and 203 are mounted on the circuit board 201 by wire bonding or die bonding.

On the other side of the circuit board 201, electrodes 204', 205' and 206' are provided which correspond to the electrodes 204, 205, and 206, respectively. Each pair of the electrodes 204 and 204', 205 and 205' and 206 and 206' are electrically connected together through a hole 207. The electrodes 204', 205' and 206' on the other side of the circuit board 201 are connected to lead wires or directly connected to another circuit board.

As shown in FIG. 14, the light emitting diodes 202 and 203 mounted on the epoxy-glass board 201 are covered with a clear epoxy resin 208. Three lead wires 209 come from the back of the board 201. The board 201 may be a 3 mm by 3 mm square with a height of 2 mm, for example.

The light emitting diodes 202 and 203 emit beams $A_1$ having a wavelength of 805 nm and beams $A_2$ having a wavelength of 940 nm, respectively. (FIG. 15).

FIG. 16 shows the seventh embodiment in which the multi-wavelength light emitter 210 and the light receptor 3 are mounted on the FPC board 1 formed with a printed wiring pattern 212. The lead wires 209 and the wiring pattern 212 are connected to the cable 15. In this embodiment, the FPC board 1 is coated with an insulating urethane resin.

In use, the FPC board 1 is put on the finger tip 7 in the manner as shown in FIG. 11 so that the light emitter 210 and the receptor 3 will oppose to each other at both sides of the finger tip 7.

Since the light emitter of the photosensor in this embodiment is of a compact one-chip type, the photosensor can be fitted easily on the finger tip or the like to measure e.g. the concentration of a specific pigment injected into the body of the examinee. Further, since the two light emitting diodes are arranged very close to each other, the beams emitted therefrom and having different wavelengths from each other can be regarded as originated from a single light source. This will simplify the signal processing.

Figure 17A:
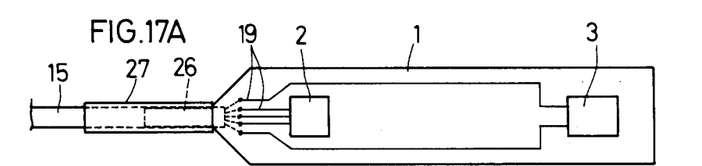
FIG. 17A is a plan view of the eighth embodiment.
Figure 17B:
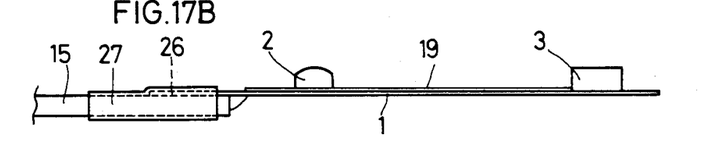
FIG. 17B is a front view of the same.

FIGS. 17A and 17B show the eighth embodiment which is a modification of the seventh embodiment. As shown in FIG. 17A, the FPC board 1 is integrally formed at its one end with a narrow strip 26. One end of the cable is put on the strip 26 and bonded thereto. A heat-shrinkable tube 27 is put on the overlapped portion and heated so as to be shrunk on the overlapped portion.

The photosensor as well as part of the heat-shrinkable tube 27 may be coated with a flexible resin to protect the entire photosensor especially its connections to wires. Such a coating has to be transparent at portions covering the beam emitting and receiving faces of the emitter and the receptor. If this coating is applied to a stick-on type sensor other than a photosensor, it may or may not be transparent.

In this embodiment, the cable has its one end overlapped with and bonded to the narrow strip of projection of the circuit board. Further, the heat-shrinkable tube is put on the overlapped portion and tightened to reinforce the bonding connection therebetween. The cable is thus less likely to get disconnected or broken. This will allow the base for the sensor elements to be made of FPC. The photosensor having an FPC base is superior in flexibility, easy to manufacture and can be fitted easily and comfortably. Still, its reliability is sufficiently high.

What is claimed is:

1. A bio-photosensor comprising:
   a flexible printed circuit board formed with an electric circuit, said flexible printed circuit board to be wrapped around a part of a body of an examinee;
   a light emitter and a light receptor mounted on said flexible printed circuit board with some distance therebetween so that said light emitter and said light receptor will be opposed to each other at both sides of said part of the examinee when said flexible printed circuit board is wrapped therearound, said light emitter and said light receptor being electrically connected through said electric circuit to an electric cable connected to one end of said flexible printed circuit board; and
   a position displacement detector means including at least a pair of sensors in a vicinity of said light receptor to check whether or not said light receptor is exactly opposed to said light emitter.

2. A bio-photosensor as claimed in claim 1, further comprising a fixing tape to be put on said flexible printed circuit board after said flexible printed circuit board has been applied to a finger so as to extend longitudinally thereof and turned back at a tip of a fingernail, said fixing tape to fix said flexible printed circuit board in position on the finger, said flexible printed circuit board being provided with a first mark at a position that said light emitter and said light receptor will be exactly opposed to each other at both sides of the finger when said bio-photosensor is applied to the finger with said first mark adapted to be in contact with the tip of the fingernail.

3. A bio-photosensor as claimed in claim 2, wherein said fixing tape is provided with second marks on a opposite side of said flexible printed circuit board at portions right behind said light emitter and said light receptor, so that said light emitter and said light receptor will be exactly opposed to each other at both sides of the finger when the bio-photosensor is applied to the finger so that said second marks will be opposed to each other at both sides of the finger.

4. A bio-photosensor as claimed in claim 2, wherein said fixing tape comprises a substrate, an adhesive layer formed on one side of said substrate and a release paper provided on said adhesive layer of protection at least one of said release paper and said substrate being provided on a surface with mounting position indicator means for said light emitter, said light receptor and a part of the body of an examinee.

5. A bio-photosensor as claimed in claim 4, wherein said mounting position indicator means for a part of the body of an examinee comprise cutouts formed at corresponding positions at both sides of said substrate and said release paper and a pattern printed at least on said release paper, and said mounting position indicator means for said light emitter and said light receptor are in a form of characters printed at least on said release paper.

6. A bio-photosensor as claimed in claim 4, wherein said release paper is formed with a perforated line or a cutline which defines an area for mounting said light emitter and said light receptor and said release paper is integrally formed with two tabs, one tab being continuous with said area and the other not.

7. A bio-photosensor as claimed in claim 1, wherein said light emitter includes a plurality of light emitting diodes each connected to respective electrodes provided on said flexible printed circuit board and to emit beams having different wavelengths from one another, one of said beams having a wavelength as to be absorbed by a specific pigment which is removed exclusively by a hepatic parenchyma when injected into blood, and another beam having wavelengths which are not to be absorbed by said pigment.

8. A bio-photosensor as claimed in claim 1, further comprising a table means provided at one end of said flexible printed circuit board, one end of a cable bonded to said tab means, and a heat-shrinkable tube to be put on an overlapped portion and shrunk to tighten said overlapped portion.

9. A bio-photosensor comprising:

a flexible printed circuit board formed with an electric circuit, said flexible printed circuit board to be wrapped around a part of a body of an examinee;

a light emitter and a light receptor mounted on said flexible printed circuit board with some distance therebetween so that said light emitter and said light receptor will be opposed so that said light emitter and said light receptor will be opposed to eac other at both sides of said part of the examinee when said flexible printed circuit board is wrapped therearound, said light emitter and said light receptor being electrically connected through said electric circuit to an electric cable connected to one end of said flexible printed circuit board, said light emitter and said light receptor are covered with a transparent material and a remaining portion other than said light emiitter and said little receptor is covered with a flexible resin; and a position displacement etector means including at least a pair of sensors in a vicinity of said light receptor to check whether or not said light receptor is exactly opposed to said light emitter.

10. A bio-photosensor as claimed in claim 9, further comprising a fixing tape to be put on said flexible printed circuit board after said flexible printed circuit board has been applied to a finger so as to extend longitudinally thereof and turned back at a tip of a fingernail, said fixing tape to fix said flexible printed circuit board in position on the finger, said flexible printed circuit board being provided with a first mark at a position that said light emitter and said light receptor will be exactly opposed to each other at both sides of the finger when said bio-photosensor is applied to the finger with said first mark adapted to be in contact with the tip of the fingernail.

11. A bio-photosensor as claimed in claim 10, wherein said fixing tape is provided with second marks on an opposite side of said flexible printed circuit board at portions right behind said light emitter and said light receptor, so that said light emitter and said light receptor will be exactly opposed to each other at both sides of the finger when the bio-photosensor is applied to the finger so that said second marks will be opposed to each other at both sides of the finger.

12. A bio-photosensor as claimed in claim 10, wherein said fixing tape comprises a substrate, an adhesive layer formed on one side of said substrate and a release paper provided on said adhesive layer for protection, at least one of said release paper and said substrate being provided on a surface with mounting position indicator means for said light emitter, said light receptor and a part of the body of an examinee.

13. A bio-photosensor as claimed in claim 12, wherein said mounting position indicator means for a part of the body of an examinee comprise cutouts formed at corresponding positions at both sides of said substrate and said release paper and a pattern printed at least on said release paper, and said mounting position indicator means for said light emitter and said light receptor are in a form of characters printed at least on said release paper.

14. A bio-photosensor as claimed in claim 12, wherein said release paper is formed with a perforated line or a cutline which defines an area for mounting said light emitter and said light receptor and said release paper is integrally formed with two tabs, one tab being continuous with said area and the other tab not being continuous.

15. A bio-photosensor as claimed in claim 9, wherein said light emitter includes a plurality of light emitting diodes each connected to respective electrodes provided on said flexible printed circuit board and to emit beams having different wavelengths from one another, one of said beams having a wavelength as to be absorbed by a specific pigment which is removed exclusively by a hepatic parenchyma when injected into blood, and another beam having wavelengths which are not to be absorbed by said pigment.

16. A bio-photosensor as claimed in claim 9, further comprising a tab means provided at one end of said flexible printed circuit board, one end of a cable bonded to said tab means, and a heat-shrinkable tube to be put on an overlapped portion and shrunk to tighten said overlapped portion.

* * * * *